(12) United States Patent
Keeler

(10) Patent No.: US 8,702,773 B2
(45) Date of Patent: Apr. 22, 2014

(54) ECCENTRIC BALLOON LASER CATHETER

(75) Inventor: Jacob Keeler, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 795 days.

(21) Appl. No.: 12/337,190

(22) Filed: Dec. 17, 2008

(65) Prior Publication Data

US 2010/0152717 A1 Jun. 17, 2010

(51) Int. Cl.
*A61N 5/06* (2006.01)

(52) U.S. Cl.
USPC .................. 607/92; 607/88; 607/89; 607/93

(58) Field of Classification Search
USPC .............................. 606/7, 14–15; 604/96.01, 604/103.01–103.11; 607/88–89, 92–93
See application file for complete search history.

(56) References Cited

U.S. PATENT DOCUMENTS

| | | | |
|---|---|---|---|
| 4,053,845 A | 10/1977 | Gould | |
| 4,445,892 A * | 5/1984 | Hussein et al. | 604/101.05 |
| 4,641,912 A | 2/1987 | Goldenberg | |
| 4,669,467 A | 6/1987 | Willett et al. | |
| 4,686,979 A | 8/1987 | Gruen | |
| 4,732,448 A | 3/1988 | Goldenberg | |
| 4,747,405 A | 5/1988 | Leckrone | |
| 4,784,132 A | 11/1988 | Fox et al. | |
| 4,799,754 A | 1/1989 | Goldenberg | |
| 4,807,620 A | 2/1989 | Sturl | |
| 4,830,460 A | 5/1989 | Goldenberg | |
| 4,844,062 A * | 7/1989 | Wells | 606/7 |
| 4,848,336 A | 7/1989 | Fox et al. | |
| 4,886,496 A * | 12/1989 | Conoscenti et al. | 604/103.11 |
| 4,924,863 A | 5/1990 | Sterzer | |
| 5,016,964 A | 5/1991 | Donnelly | |
| 5,041,108 A | 8/1991 | Fox et al. | |
| 5,042,976 A * | 8/1991 | Ishitsu et al. | 604/96.01 |
| 5,188,632 A | 2/1993 | Goldenberg | |
| 5,250,045 A | 10/1993 | Bohley | |
| 5,263,952 A | 11/1993 | Grace et al. | |
| 5,304,171 A | 4/1994 | Gregory | |
| 5,350,375 A | 9/1994 | Deckelbaum et al. | |
| 5,352,197 A | 10/1994 | Hammersmark | |
| 5,415,653 A | 5/1995 | Wardle | |
| 5,429,604 A | 7/1995 | Solar et al. | |

(Continued)

OTHER PUBLICATIONS

International Preliminary Report on Patentability for International (PCT) Patent Application No. PCT/US2009/065557, mailed Jun. 30, 2011.

(Continued)

*Primary Examiner* — Bhisma Mehta
*Assistant Examiner* — William Cheng
(74) *Attorney, Agent, or Firm* — Sheridan Ross P.C.

(57) ABSTRACT

Various embodiments of an eccentric balloon catheter are disclosed. In some embodiments, an eccentric balloon catheter includes an eccentrically positioned guidewire tube, with an interior lumen, that extends at least a portion of the length of the catheter body. Optical fibers may extend the length of the catheter body and may also be eccentrically positioned within the catheter body. An inflatable balloon may be positioned within a window within the catheter body near the distal end of the catheter. When inflated, the balloon and catheter may slide relative to one another. When used within a vessel, an inflated balloon may press against a vessel wall and bias the catheter toward an opposite vessel wall.

23 Claims, 12 Drawing Sheets

(56) References Cited

U.S. PATENT DOCUMENTS

| | | |
|---|---|---|
| 5,429,617 A | 7/1995 | Hammersmark |
| 5,456,680 A | 10/1995 | Taylor et al. |
| 5,470,330 A | 11/1995 | Goldenberg |
| 5,484,433 A | 1/1996 | Taylor et al. |
| 5,514,128 A | 5/1996 | Kasprzyk et al. |
| 5,571,151 A | 11/1996 | Gregory |
| 5,573,531 A | 11/1996 | Gregory |
| 5,623,940 A | 4/1997 | Daikuzono |
| 5,643,251 A | 7/1997 | Kasprzyk et al. |
| 5,649,923 A | 7/1997 | Gregory |
| 5,722,972 A | 3/1998 | Power et al. |
| 5,817,144 A | 10/1998 | Gregory |
| 5,824,026 A | 10/1998 | Diaz |
| 5,836,946 A | 11/1998 | Diaz |
| RE36,104 E | 2/1999 | Solar |
| 5,976,124 A | 11/1999 | Reiser |
| 5,989,243 A | 11/1999 | Goldenberg |
| 6,022,342 A | 2/2000 | Mukherjee |
| 6,066,130 A | 5/2000 | Gregory |
| 6,117,128 A | 9/2000 | Gregory |
| 6,290,668 B1 | 9/2001 | Gregory |
| 6,458,098 B1 | 10/2002 | Kanesaka |
| 6,613,038 B2 * | 9/2003 | Bonutti et al. ............... 604/509 |
| 6,743,208 B1 | 6/2004 | Coyle |
| 2006/0206182 A1 * | 9/2006 | Pyles .......................... 607/117 |
| 2007/0270787 A1 | 11/2007 | Winston et al. |
| 2008/0154345 A1 | 6/2008 | Taylor |

OTHER PUBLICATIONS

PCT International Search Report and Written Opinion mailed Jan. 26, 2010; International Application No. PCT/US2009/065557; 12 pages.

Extended Search Report for European Patent Application No. 09833795.9, dated Apr. 12, 2012 6 pages.

Official Action for European Patent Application No. 09833795.9, dated Nov. 20, 2012 4 pages.

* cited by examiner

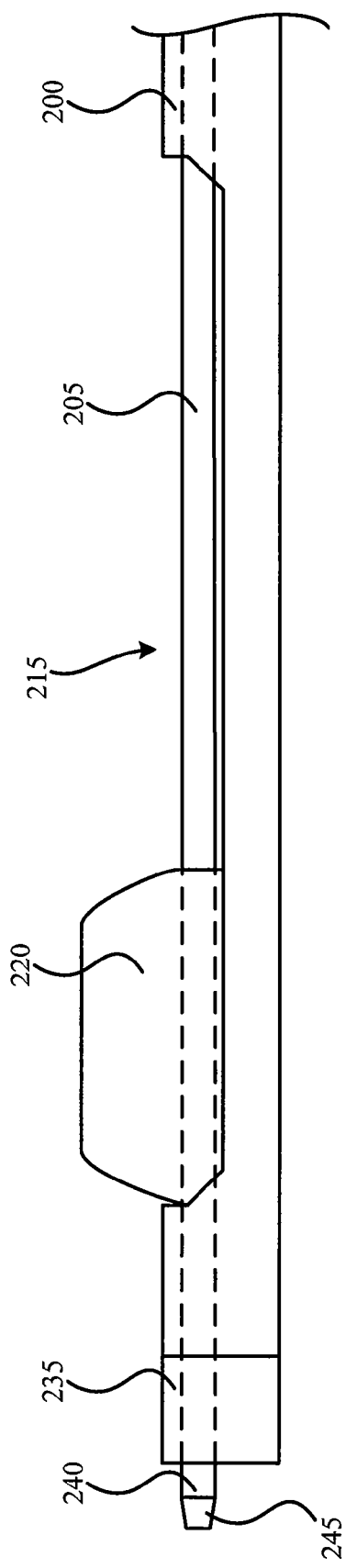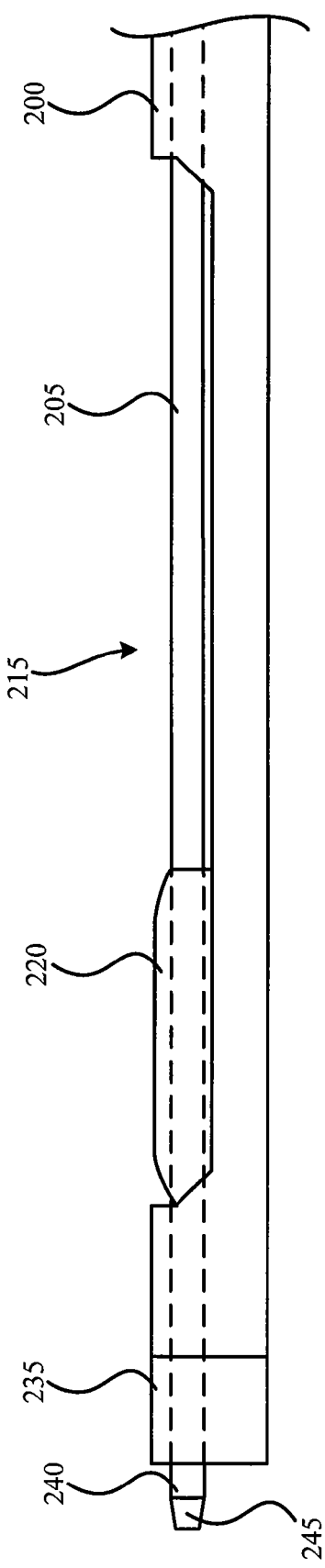
FIG. 3A
FIG. 3B

ECCENTRIC BALLOON LASER CATHETER

BACKGROUND

The embodiments described herein are generally directed to improved apparatus and methods for the delivery of laser energy, including without limitation, to a laser delivery catheter.

Arteries are the primary blood vessels that are responsible for providing blood and oxygen to the heart muscle. Arterial disease occurs when arteries become narrowed or blocked by a buildup of plaque (as some examples, atherosclerotic plaque or other deposits). When the blockage is severe, the flow of blood and oxygen to the heart muscle is reduced, causing chest pain. Arterial blockage by clots formed in a human body may be relieved in a number of traditional ways. Drug therapy, including nitrates, beta-blockers, and peripheral vasodilatator drugs to dilate the arteries or thrombolytic drugs to dissolve the clot, can be effective. If drug treatment fails, angioplasty may be used to reform or remove the atherosclerotic plaque or other deposits in the artery.

Traditional balloon angioplasty is sometimes used to address the blockage by inserting a narrow, flexible tube having a balloon into an artery in the arm or leg. The blocked area in the artery can be stretched apart by passing the balloon to the desired treatment site and gently inflating it a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion thereby requiring emergency procedures), the procedure known as excimer laser angioplasty may be indicated.

Excimer laser angioplasty procedure is similar in some respects to conventional coronary balloon angioplasty. A narrow, flexible tube, the laser catheter, is inserted into an artery in the arm or leg. The laser catheter contains one or more optical fibers, which can transmit laser energy. The laser catheter is then advanced inside the artery to the targeted obstruction at the desired treatment site. After the laser catheter has been positioned, the laser is energized to "remove" the obstruction.

In many procedures, the lesion is often engaged similar to conventional balloon angioplasty by crossing the blockage with a guidewire. The laser catheter's thin, flexible optical fibers facilitate the desired positioning and alignment of the catheter. Using the excimer laser, the clinician performs a controlled blockage removal by sending bursts of ultraviolet light through the catheter and against the blockage, a process called "ablation." The catheter is then slowly advanced through the blockage reopening the artery. If there are multiple blockages, the catheter is advanced to the next blockage site and the above step is repeated. When the indicated blockages appear to be cleared, the catheter is withdrawn.

However, due to the configuration of the optical fibers in most prior art laser catheters, the clinician is able to ablate only material that is typically directly in front of the distal end of the catheter. Thus, the debulked tissue area is limited to an area approximately the size of the optical fiber area at the distal end of the catheter. Typically, follow-up angioplasty is recommended.

Thus, it would be desirable to provide an apparatus and methods that could bias the distal end of the laser catheter in a desired direction to enable the clinician to ablate an area larger than the area of the distal end of the catheter. Furthermore, because plaque may be eccentric in a blood vessel and require directional control to adequately ablate the target area, it would be advantageous to provide an apparatus that is sufficiently flexible to travel and rotate around the target area so that the clinician may control the area to be ablated.

BRIEF SUMMARY

A laser catheter is provided according to one embodiment that includes a catheter body, a light guide, an inner tube and a balloon. The catheter body may include a central axis, a distal end, a proximal end, and a cavity disposed proximate to the distal end. The inner tube may include an port at the distal end of the catheter body and the inner tube positioned eccentric relative to the longitudinal central axis of the catheter body. The light guide may be disposed within the catheter body and may extend from the proximal end to the distal end of the catheter body. The balloon may be disposed within the cavity and slidably coupled with the catheter body allowing the catheter body to move relative to the balloon, and allowing the balloon to move relative to the catheter body.

A laser catheter is provided according to another embodiment that includes a catheter body, a guidewire tube, a light guide tube, and at least one fiber optic. The catheter body may include central axis (for example, a longitudinal central axis), a distal end, a proximal end, and a window disposed on the periphery of the catheter body proximate to the distal end. The guidewire tube may include an inner lumen located eccentrically within the catheter body and an aperture at the distal end of the catheter body. The light guide tube may have an inner lumen located eccentrically within the catheter body The light guide tube may also include an aperture at the distal end of the catheter body. The light guide tube may extend from the proximal end of catheter body to the distal end of the catheter body. The at least one fiber optic may be disposed within the inner lumen of the light guide tube and extend the length of the light guide tube. The inflatable balloon may be disposed within the window of the catheter body.

In some embodiments, the laser catheter may include a straightening stylet coupled with the catheter body proximate to the cavity. In some embodiments, the balloon surrounds the inner tube. In some embodiments, a balloon rail may be coupled with the balloon and the catheter body. The balloon rail may be configured to allow the balloon to slide relative to the catheter body. In some embodiments, the laser catheter may also include a balloon tube disposed within the catheter body, coupled with the balloon, and configured to provide air to the balloon. In some embodiments, the cavity may be disposed within the periphery of the catheter body. In some embodiments, the cavity may be disposed proximate the inner tube, such that the inner tube is at least partially exposed by the cavity. In some embodiments, the light guide may include at least one optical fiber. In some embodiments, the inner tube may extend from the proximal end toward the distal end of the catheter body.

Further areas of applicability of the present disclosure will become apparent from the detailed description provided hereinafter. It should be understood that the detailed description and specific examples, while indicating various embodiments, are intended for purposes of illustration only and do not limit the scope of the disclosure.

BRIEF DESCRIPTION OF THE DRAWINGS

FIGS. 3A and 3B show an eccentric balloon catheter with the balloon inflated and deflated according to some embodiments.

Figure 1:
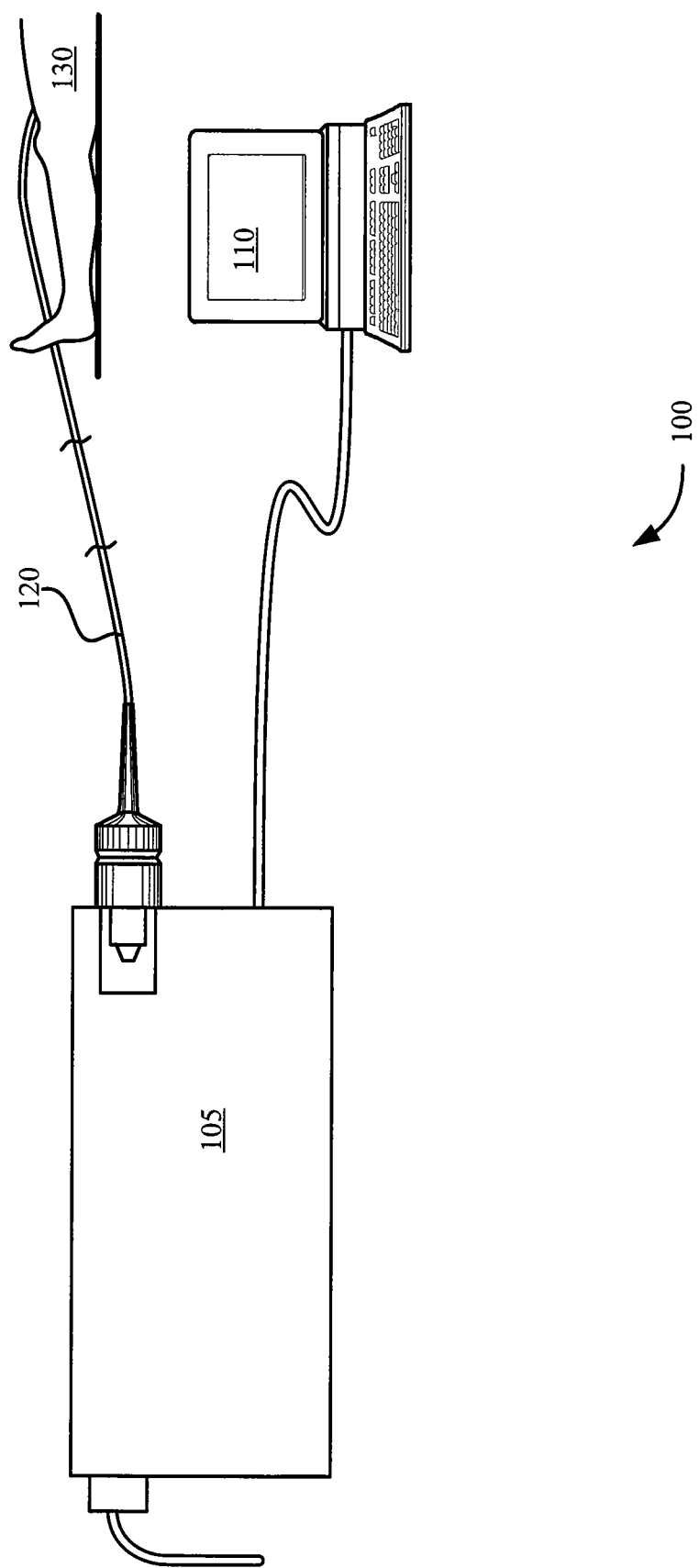
FIG. 1 shows a catheter system according to one embodiment of the invention.

In the appended figures, similar components and/or features may have the same reference label. Where the reference label is used in the specification, the description is applicable to any one of the similar components having the same reference label. Moreover, the figures are not drawn to scale. For example, some components may not be drawn to scale relative to other components.

DETAILED DESCRIPTION

The ensuing description provides various embodiments of the invention only, and is not intended to limit the scope, applicability or configuration of the disclosure. Rather, the ensuing description of the embodiments will provide those skilled in the art with an enabling description for implementing an embodiment. It should be understood that various changes may be made in the function and arrangement of elements without departing from the spirit and scope as set forth in the appended claims.

Embodiments described herein provide for an eccentric balloon catheter. A catheter is provided that includes an elongated catheter body with a cavity (or window) within a peripheral portion of the elongated catheter body near the distal end of the catheter. The cavity exposes a portion of the interior of the catheter body and/or may extend along a portion of the periphery of the catheter body. A balloon may be disposed within the catheter body within the cavity such that when the balloon is deflated or mostly deflated the balloon is contained within the radius of catheter body. When the balloon is inflated the balloon expands and extend through the cavity beyond a portion of the periphery of the catheter body. Moreover, in some embodiments, the balloon may eccentrically located within the catheter body, such that when inflated the balloon inflates generally outwardly in one direction from the axis of the catheter body. In some embodiments, the balloon may be coupled with the catheter body such that the balloon and the elongate housing may move relative to one another.

An eccentric balloon catheter may also include an eccentric guidewire tube that extends at least to the distal end of the catheter and have an aperture at the distal face of the catheter. The eccentric guidewire tube may be positioned eccentric relative to the central axis of the catheter body. Moreover, the guidewire tube may include an inner lumen. The guidewire tube may also extend to the proximal end of the catheter or the guidewire tube may terminate anywhere along the elongated catheter body with a proximal aperture. The guidewire tube, for example, may have an outer diameter of 0.024 inches and an inner diameter of 0.018 inches. The guidewire tube may generally be configured to accept a guidewire and allow the guidewire to slide within the guidewire lumen. The guidewire tube may also be eccentrically arranged within the catheter body. That is, the guidewire tube may not be aligned with the longitudinal central axis of the catheter body, instead, the guidewire tube may be offset between the catheter body central axis and the periphery of the catheter body. In some embodiments, the guidewire tube may be eccentrically located near the same periphery as the cavity. That is, the guidewire tube may extend along a portion of the length of the catheter body parallel to the central axis of the catheter body but off axis with respect to the central axis. In some embodiments, the guidewire tube within the cavity may be exposed to the exterior of the elongate housing. The catheter body may also include one or more light guides, for example, such as a plurality of optical fibers arranged to conduct light from the proximal end of the catheter toward the distal end of the catheter.

Figure 9A:
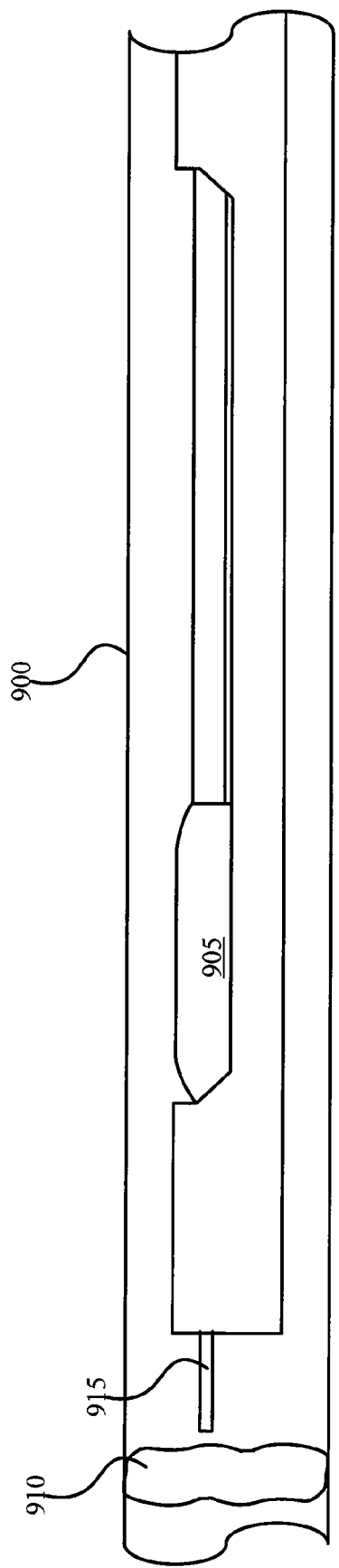
FIGS. 9A, 9B and 9C show an eccentric balloon catheter in various positions within a vessel according to some embodiments.
Figure 9B:
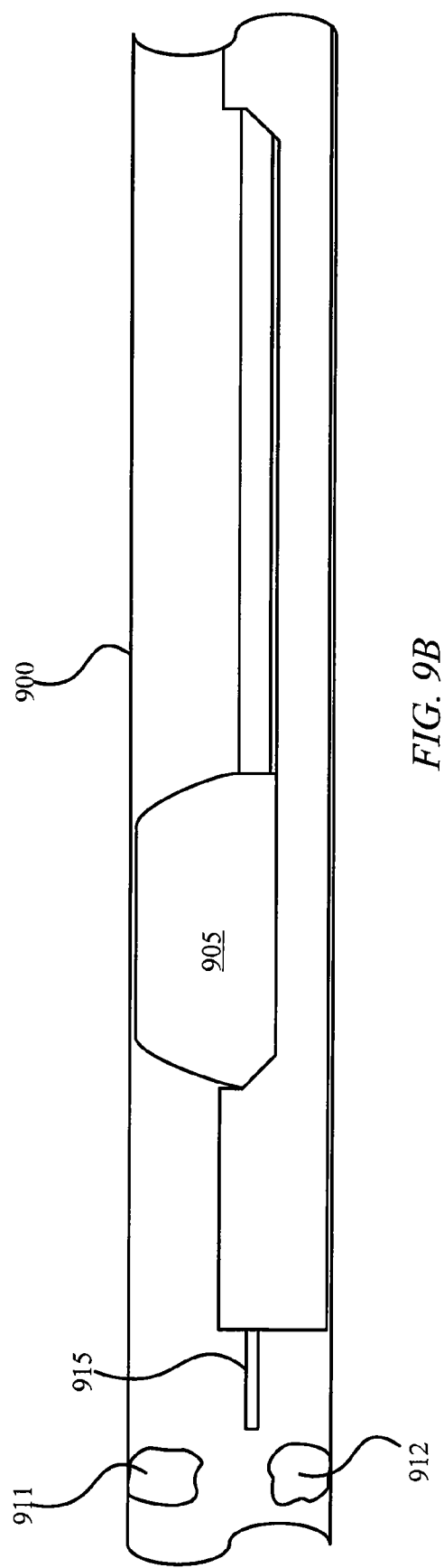

In use, the eccentric balloon catheter may be inserted into a vessel within the human body by following a previously placed guidewire through the guidewire lumen (as shown in FIG. 9A). Once the distal end of the catheter is positioned near a target within the vessel, the catheter may ablate a portion of the target with laser light. The size of the resulting ablation will be at most the diameter of the distal aperture of the fiber optic bundle. In order to ablate a larger cross section within the target, the balloon may be inflated. As the balloon is inflated, the balloon may provide pressure against an inner vessel wall, which may move the catheter laterally within the vessel (as shown in FIG. 9B). After the catheter has moved laterally, the exit aperture of the light guide is now positioned to ablate a previously unablated portion of the target. The balloon may be deflated, the catheter twisted along the central axis, and the balloon inflated to position the exit aperture of the light guide near another unablated portion of the target. If the exit aperture of the light guide is not close enough to the target or too close to the target, the catheter may slide longitudinally relative to the balloon to move into a more ideal position.

FIG. 1 shows a eccentric balloon catheter 100 in use according to one embodiment of the invention. Laser 105 is shown coupled with user interface 110. Laser 105 and user interface 110, in other embodiments of the invention, may be coupled into one system. Laser 105 is connected with catheter 120 that may be inserted into a vessel within a human body 130. Laser 105 and catheter 120 may be coupled using a laser coupler. Catheter 120 may include an elongated tube that may include a number of elements. Catheter 120 may be of any suitable length A, with a length A between about 50 cm and about 390 cm. For example, the catheter may be 0.04 inches to 0.16 inches in diameter. Catheter 120 may include at least one optical fiber or a bundle of optical fibers that transmits light from laser 105 down at least a portion of the catheter. Some optical fibers may return reflected light back toward laser 105.

The fiber optics within the catheter may receive light from the laser and conduct the light from the proximal end of the catheter to a target from the distal end of the catheter. The catheter may also use liquid or a combination of liquid and optical fibers to conduct light toward the distal end. The light from the laser may be directed toward a target within a vessel using fiber optics within the catheter. The target may be within various biological vessels, for example, blood vessels, arteries, capillaries, organs, etc. In non medical applications, for example, the vessel may include any type a deep cavity within which non-destructive imaging is required, such as, tubes, chambers, pipes, etc.

Figure 2:
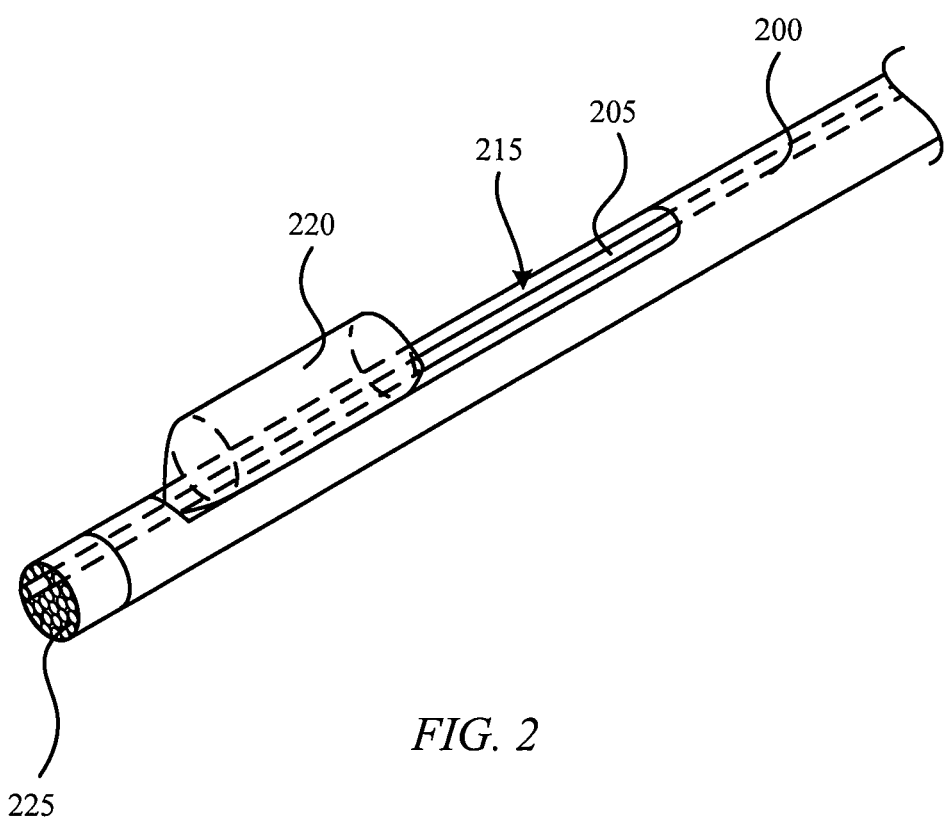
FIG. 2 shows eccentric balloon catheter according to some embodiments.

FIG. 2 shows eccentric balloon catheter including a catheter body 200 with cavity 215 cut through a portion of the periphery of the catheter body. Catheter body 200 may also include distal end 225. Cavity 215 may extend longitudinally for about 1 cm, 5 cm, 10 cm or more along the periphery of the elongated body. Cavity 215 may simply be cut from the periphery of the catheter body and/or may expose portions of the catheter within catheter body 200. Cavity 215 is position on one side of catheter body 200. A guidewire tube 205 may include a guidewire lumen disposed therein and may be disposed within catheter body 200. Guidewire tube 205, for example, may extend to distal end 225 of catheter body 200. At distal end 225, guidewire tube 205 may have an exit port wherein a guidewire may be introduced and slid through the guidewire lumen. Distal end 225 also shows the distal ends of a plurality of fiber optics that extend through the catheter body from the proximal end toward the distal end. The fiber optics may be disposed within the catheter body opposite the guidewire tube. The fiber optics may be replaced with any material that transmits laser light from the proximal end toward the distal end. For example, a liquid light guide may be used singly or in combination with fiber optics.

Balloon 220 is shown inflated and extending from within cavity 215. Balloon 220 may have a diameter of about 2 mm to 4 mm when inflated, according to one embodiment. In some embodiments, balloon 220 may have an inflated diameter up to about 6 mm and as little as 1 mm. In some embodiments, balloon 220 may comprise tubing with a sealed distal end. In some embodiments, the distal end of balloon tubing may have thinner walls and/or a larger diameter such that the distal end inflates under pressure. Balloon 220, for example, may comprise any type of plastic, for example, balloon 220 may comprise nylon, Teflon, urethane, polyethylene, or a mixture thereof. Balloon 220, in some embodiments, may be 10 cm, 9 cm, 8 cm, 7 cm, 6 cm, 5 cm, 4 cm, 3 cm, 2 cm, or 1 cm in length. In some embodiments, balloon 220 may be partially inflated, completely inflated, completely deflated or any level of inflation/deflation in between. Moreover, in some embodiments, balloon 220 may be a compliant balloon which allows for varying inflation diameters without full inflation. In other embodiments, balloon 220 may be non-compliant.

Balloon 220 may also be coupled with a balloon lumen (or balloon tube with an inner lumen) that extends from the proximal portion of the balloon through the catheter body toward the proximal end of the guidewire housing. Balloon lumen may terminate at a balloon port. Balloon lumen may couple with a luer fitting at balloon port. In some embodiments, balloon lumen may bifurcate with the catheter body and be located a distance away from the catheter body. Balloon lumen may include a small diameter lumen. For example, the inner diameter of balloon lumen may be approximately 0.007 inches. In some embodiments, the inner diameter of balloon lumen may be between 0.005 and 0.015 inches. The outside diameter of balloon lumen, for example, may be 0.016 inches. In some embodiments, the outside diameter of balloon lumen may be 0.05 to 0.007 inches. At the balloon port or luer, balloon lumen may be coupled with a syringe or an indeflator. Balloon 220 may be inflated by injecting fluid through balloon lumen using either a syringe or an indeflator. In some embodiments, the balloon may be inflated using a contrast agent fluid or saline solution. Balloon lumen may include any type of plastic tubing known in the art. For example, balloon lumen may comprise nylon, urethane, Teflon, polyethylene, etc.

FIG. 3A shows an eccentric balloon catheter with an inflated balloon 220. In some embodiments, when balloon 220 is inflated it extends through cavity 215 (window) past the periphery of the catheter's catheter body 200. FIG. 3B shows an eccentric balloon catheter with a deflated balloon 220. In some embodiments, when balloon 220 is deflated it remains and/or is contained within the periphery of the catheter's catheter body 200 within cavity 215. Balloon 220 may be coupled with a balloon lumen. Balloon 220 inflation tube may then be coupled with an air or liquid pump. The balloon may be inflated by the pump by pumping air or liquid into the balloon. In some embodiments, balloon 220 may be deflated by removing the air or liquid from balloon 220 using the pump. In some embodiments, because balloon 220 is pressurized when inflated, balloon 220 may be deflated by purging the air or liquid from the balloon with or without using the pump. For example, a purge valve may be coupled with the balloon lumen that allows the air or liquid within an inflated balloon to be released when the purge valve is opened.

In some embodiments, balloon 220 may also surround guidewire tube 205. In other embodiments, balloon 220 may be coupled with guidewire tube 205 but does not surround guidewire tube 205.

Figure 4A:
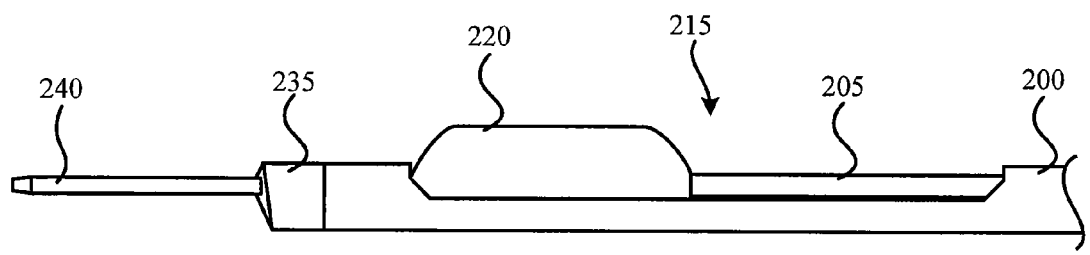
FIGS. 4A and 4B show the slidability of an eccentric balloon catheter according to some embodiments.
Figure 4B:
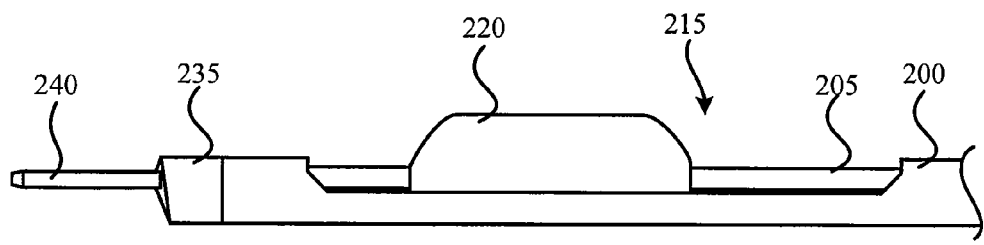

FIGS. 4A and 4B show the slidability of an eccentric balloon catheter according to some embodiments. FIG. 4A shows balloon 220 in a first position near the distal end of cavity 215. FIG. 4B shows balloon 220 in a second position near the middle of cavity 215. As shown, balloon 220 may slide relative to catheter body 200. Moreover, catheter body 200, including a light guide disposed therein and or guidewire tube 205, may move relative to balloon 220. Hence, catheter body 200 with the light guide may be advanced over a guidewire toward a target while balloon 220 is inflated and held relatively in position.

Figure 8:
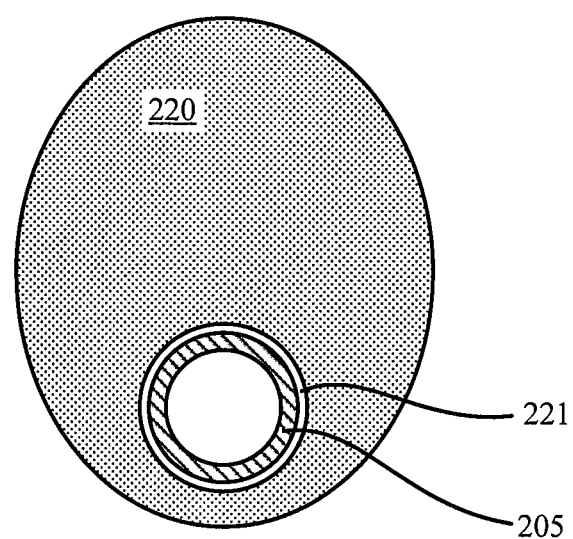
FIG. 8 shows a cut away of an eccentric balloon surrounding a guidewire tube according to one embodiment.

In some embodiments, balloon 220 is coupled with a rail and/or track system that enables balloon 220 and catheter body 200 to slide relative to one another. For example, as shown in FIG. 8, guidewire tube 205 may include a stiff and/or slick exterior surface that, at least within cavity 215. Balloon 220 may include an inner lumen 221 that slides over guidewire tube 205. In some embodiments, guidewire tube 205 may have a slick or lubricated surface to allow balloon lumen 221 to slide relative to guidewire tube 205. In some embodiments, balloon 220 and catheter body 200 may be coupled with a plunger, such as a spring loaded plunger, at the proximal end of the eccentric balloon catheter, which may be used to actuate balloon 220 relative to catheter body 200.

Figure 5A:
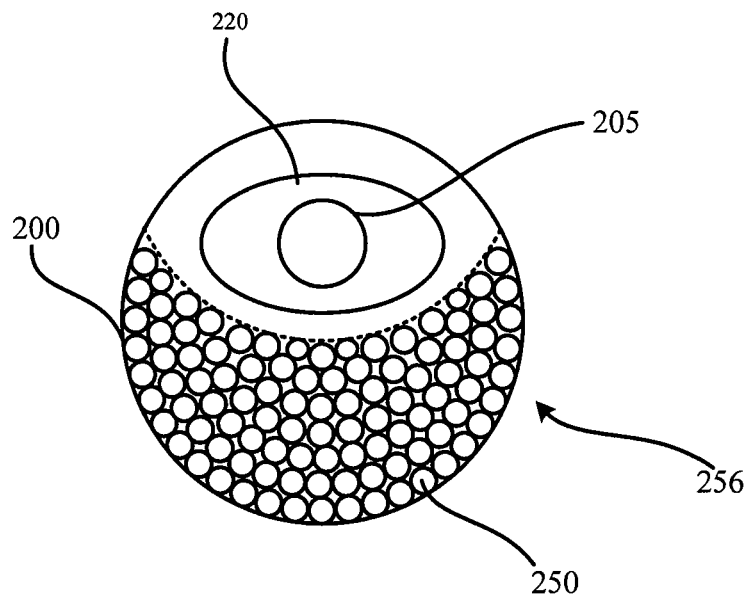
FIG. 5 show a distal end view of an inflated and deflated eccentric balloon catheter according to some embodiments.
Figure 5B:
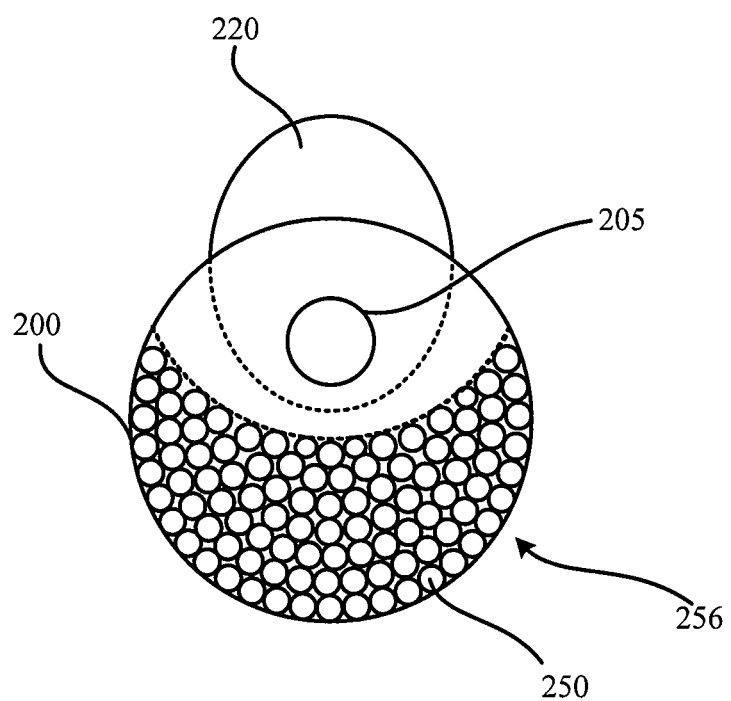

FIG. 5A show a distal end view of deflated eccentric balloon catheter according to some embodiments. As shown in some embodiments, balloon 220 is contained within the periphery of catheter body 200 when deflated. Also, in some embodiments, balloon 220 is surrounds guidewire tube 205. FIG. 5B shows a distal end view of inflated eccentric balloon catheter. As shown in some embodiments, balloon 220 extends outside the periphery of catheter body 200 when inflated. Both figures also show the distal ends of a plurality of fiber optics 250 arranged in a bundle. Fiber optics 250, in some embodiments, may be contained within light guide lumen 256 that separates them from cavity 215 and/or guidewire tube 205. In some embodiments, fiber optics 250 may not be contained within a lumen and, therefore, a portion of fiber optics 250 may be exposed by cavity 215.

Figure 6:
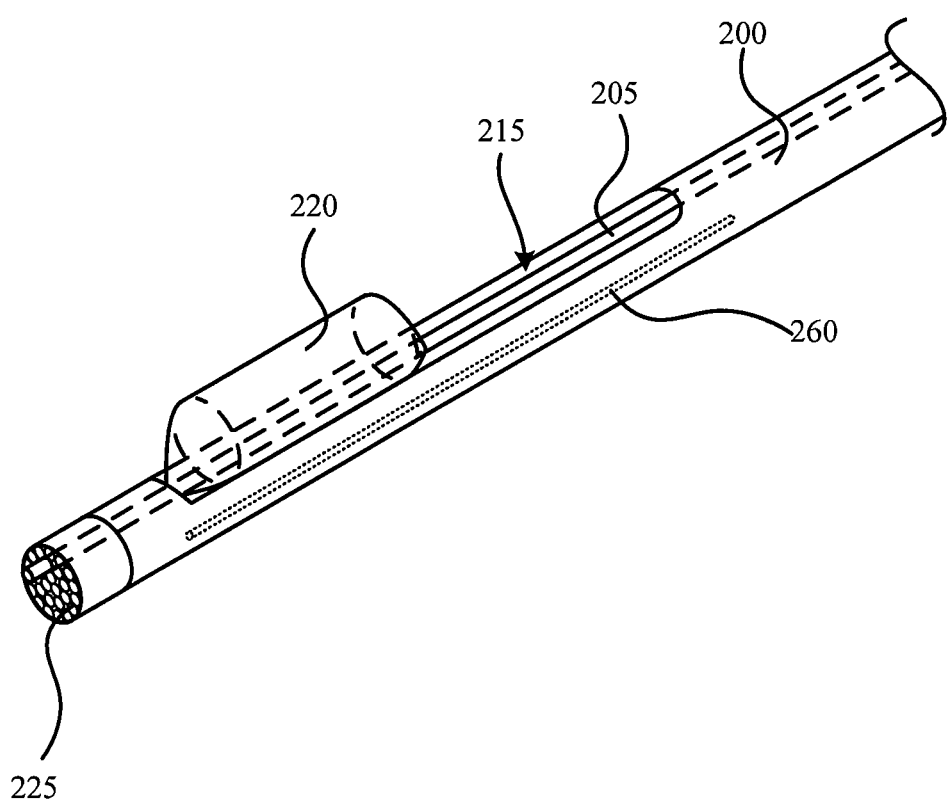
FIG. 6 shows an eccentric balloon catheter with a straightening stylet included within the catheter according to some embodiments.

FIG. 6 shows an eccentric balloon catheter with a straightening stylet (or rib) 260 included within the catheter according to some embodiments. Straightening stylet 260 may provide added support to the portion of catheter body 200 near cavity 215. Moreover, straightening stylet 260 may provide structural strength, stiffness, and/or keep the distal end of catheter body 200 and the catheter from bending. Straightening stylet 260 may also ensure proper biasing of the distal end of the catheter when balloon 220 is inflated. In some embodiments, straightening stylet 260 may be coupled with catheter body 200. In some embodiments, straightening stylet 260 may be inserted within the catheter during use. In some embodiments, straightening stylet 260 may be inserted within catheter body 200 after inflation of balloon 220.

Figure 7:
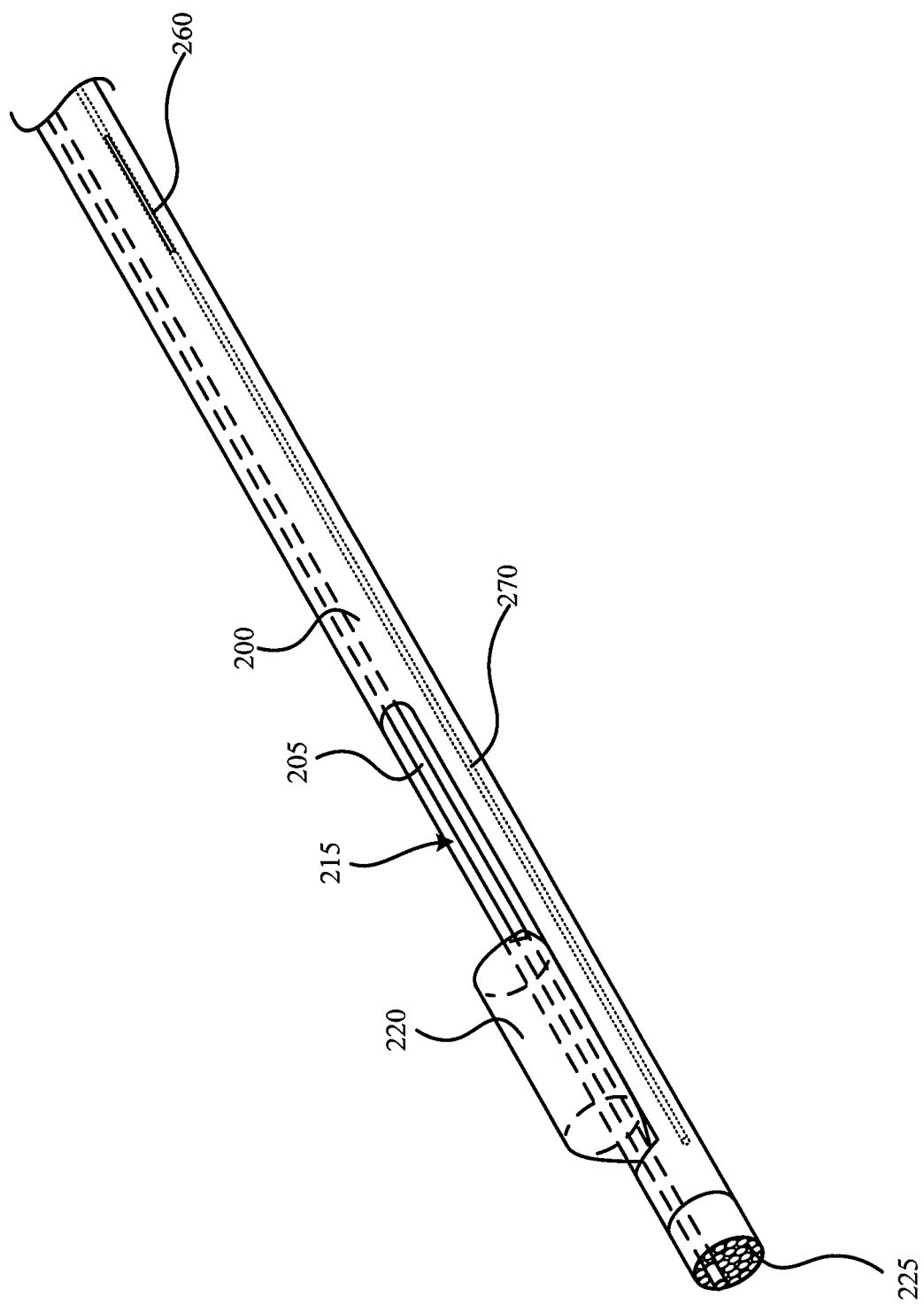
FIG. 7 shows an eccentric balloon catheter with a stylet lumen according to some embodiments.

In some embodiments, eccentric balloon catheter may include stylet lumen 270 disposed, for example, within catheter body 200 and/or within the light guide, as shown in FIG. 7. For example, stylet lumen 270 may be disposed within a fiber optic bundle. Straightening stylet 260 may be located within the proximal end of the stylet lumen 270 prior to use. In use, straightening stylet 260 may be moved toward the distal end of the eccentric balloon catheter, for example, near cavity 215 to provide stiffness to the portion of catheter body 200 near cavity 215. Stylet lumen 270 and/or straightening stylet 260 may be coupled with a plunger to move straightening stylet 260 toward the distal end of the catheter.

Figure 9C:
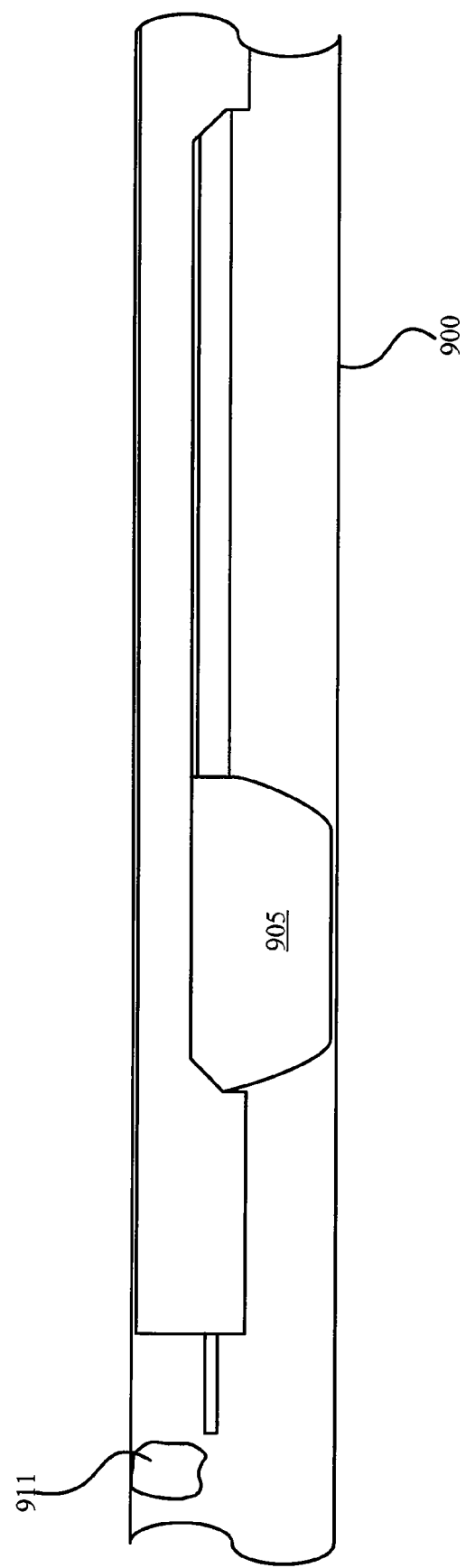

FIG. 9A shows an eccentric balloon laser catheter positioned near target 910 within a vessel 900 with balloon 905 deflated. Eccentric balloon laser catheter may be positioned using guidewire 915. In position, eccentric laser catheter may ablate at least a portion of target 910. FIG. 9B shows target 910 ablated through the middle leaving two portions of target 911, 912. Moreover, FIG. 9B shows eccentric balloon 905 inflated and pressed against a wall of vessel 900 shifting eccentric balloon laser catheter within vessel 900. In this position, eccentric balloon laser catheter may ablate target portion 912. Balloon 905 may be deflated, eccentric balloon laser catheter may be rotated, for example, about 180°, and balloon 905 inflated, as shown in FIG. 9C. In this position, target portion 911 may be ablated. In some embodiments, the catheter or the light guide may be advanced relative to balloon 905.

Figure 10:
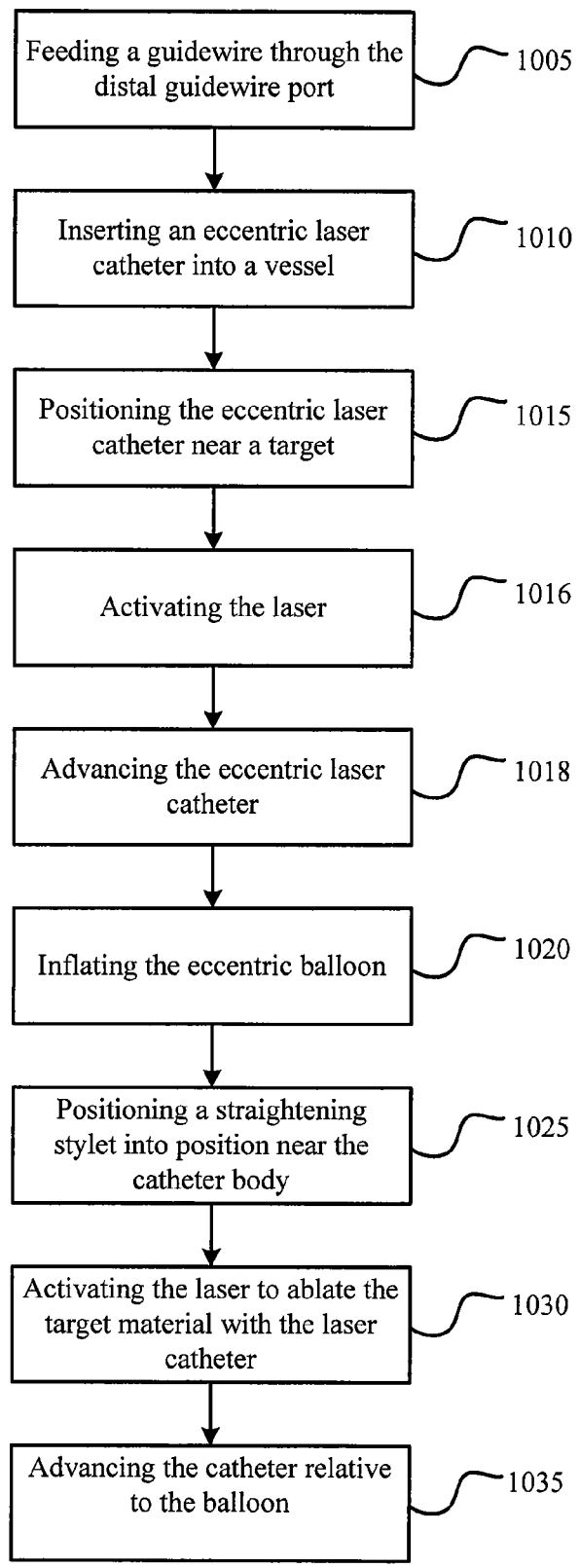
FIG. 10 shows a flowchart depicting a method for using a balloon catheter according to some embodiments.
Figure 11:
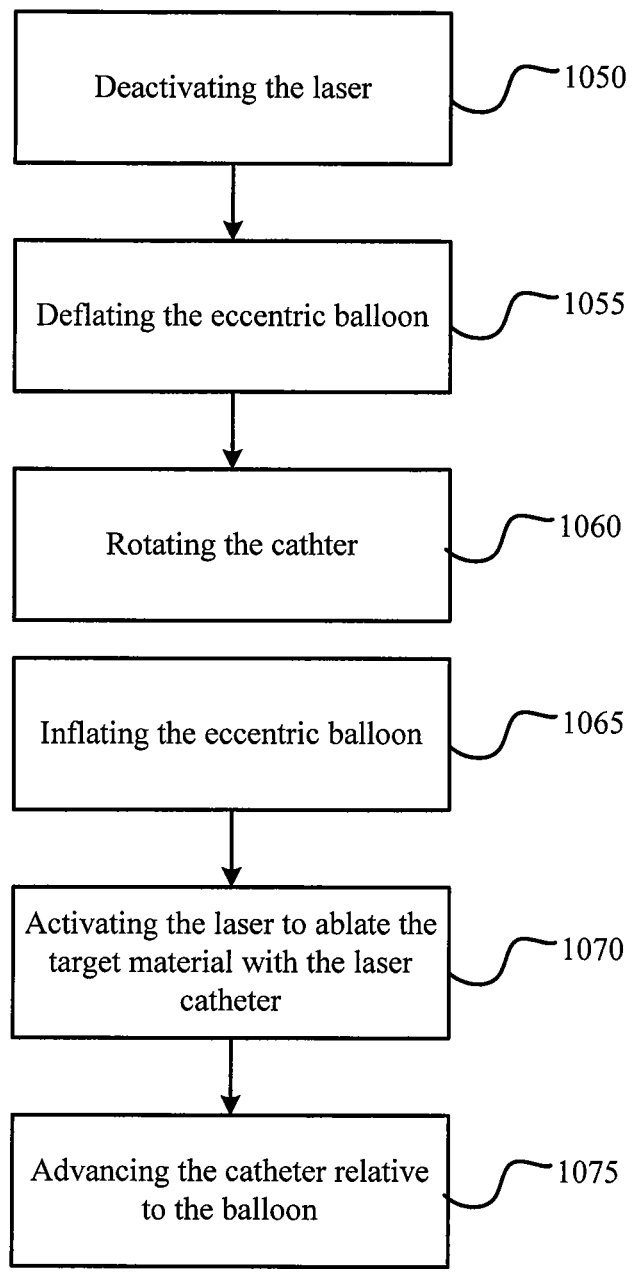
FIG. 11 shows another flowchart depicting a method for using a balloon catheter according to some embodiments.

FIG. 10 shows a flowchart of a method of using an eccentric balloon catheter according to one embodiment. Some steps may be omitted and others added to what is shown in FIG. 10 and/or what is described herein. The proximal end of a guidewire is fed, for example, through a guidewire lumen starting at the guidewire port at block 1005. The guidewire may have been previously positioned within the vessel. The catheter may then be inserted into the vessel by feeding the catheter over the guidewire tube until the catheter is positioned at or near a target at blocks 1010 and 1015. Once at the target, the laser may be activated at block 1016, and the eccentric balloon catheter may be advanced through the lesion ablating a portion of the target at block 1018, creating a pilot channel. Once the pilot channel has been ablated the laser catheter may be deactivated and/or repositioned. In order to ablate the periphery of the target and/or the pilot channel, for example, the eccentric balloon may be inflated causing the catheter to axially shift within the vessel at block 1020. Because of this axially shift, the distal end of the catheter may not be in position to ablate material near the vessel walls. Accordingly, at block 1025, a stiffening stylet may be inserted into the catheter to provide lateral support near where the balloon is exerting pressure. The stiffening stylet may inserted at anytime during the procedure. The laser may then be activated ablating target material at block 1030 and the catheter may optionally be advanced while the balloon is held relatively in place at block 1035.

What is claimed is:

1. A laser catheter comprising:
   a catheter body including a central axis, a distal end, a proximal end, and a cavity disposed within a periphery of the catheter body proximal to the distal end, wherein the cavity is cut through a portion of the periphery of the catheter body;
   an inner tube including a port at the distal end of the catheter body, the inner tube positioned eccentric relative to the central axis of the catheter body;
   a light guide disposed within the catheter body and extending from the proximal end to the distal end; and
   a balloon disposed within the cavity, wherein the balloon is configured to inflate inside the cavity, wherein a portion of the inflated balloon extends outside of the cavity proximal to the distal end of the catheter body, and wherein the inflated balloon is slidably coupled with the catheter body allowing the catheter body to move relative to the inflated balloon and allowing the inflated balloon to move relative to the catheter body in a longitudinal direction of the central axis, the inflated balloon remaining proximal to the distal end of the catheter body.

2. The laser catheter according to claim 1, further comprising a straightening stylet coupled with the catheter body proximate to the cavity.

3. The laser catheter according to claim 1, wherein the balloon surrounds at least a portion of the inner tube.

4. The laser catheter according to claim 1, wherein the balloon includes an inner lumen and at least a portion of the inner lumen surrounds at least a portion of the inner tube.

5. The laser catheter according to claim 1, further comprising a balloon tube disposed within the catheter body, coupled with the balloon, and configured to provide air to the balloon.

6. The laser catheter according to claim 1, wherein the cavity is disposed proximate the inner tube, such that the inner tube is at least partially exposed by the cavity.

7. The laser catheter according to claim 1, wherein the light guide comprises at least one optical fiber.

8. The laser catheter according to claim 1, wherein the inner tube extends from the proximal end toward the distal end of the catheter body.

9. The laser catheter according to claim 1, further comprising a laser coupled with a proximal end of the light guide.

10. A laser catheter comprising:
    a catheter body including a central axis, a distal end, a proximal end, and a window disposed on a periphery of the catheter body proximal to the distal end, wherein the window exposes a portion of an interior of the catheter body;
    a guidewire tube having an inner lumen located eccentrically within the catheter body and including an aperture at the distal end of the catheter body, a light guide tube having an inner lumen located eccentrically within the catheter body, the light guide tube including an aperture at the distal end of the catheter body, the light guide tube comprising a length extending from the proximal end of the catheter body to the distal end of the catheter body;
    at least one fiber optic disposed within the inner lumen of the light guide tube and extending the length of the light guide tube; and
    an inflatable balloon disposed within the window of the catheter body, wherein the inflatable balloon is configured to inflate within the window, wherein a portion of the inflated inflatable balloon extends through the window, and wherein the inflated inflatable balloon remains proximal to the distal end of the catheter body.

11. The laser catheter according to claim 10, further comprising a balloon inflation lumen coupled with the balloon and extending at least through a portion of the catheter body.

12. The laser catheter according to claim 10, wherein the balloon is slidably coupled with the catheter body.

13. The laser catheter according to claim 10, wherein the balloon is slidably coupled with the guidewire tube.

14. The laser catheter according to claim 10, wherein the guidewire tube extends through the window and is exposed thereby.

15. The laser catheter according to claim 10, further comprising a straightening stylet coupled with the catheter body proximate to the window.

16. The laser catheter according to claim 10, wherein when the balloon is substantially deflated the balloon fits substantially within the window.

17. The laser catheter according to claim 10, wherein when the balloon is substantially inflated the balloon extends beyond the limits of the window.

18. The laser catheter according to claim 10, wherein when the balloon is substantially inflated the balloon extends through the window beyond a radius of a portion of the catheter body.

19. The laser catheter according to claim 10, wherein when the balloon is substantially deflated the balloon is disposed within a radius of the catheter body.

20. The laser catheter according to claim 10, wherein the portion of the interior of the catheter body is exposed when the inflatable balloon is inflated.

21. The laser catheter according to claim 20, wherein the portion of the interior of the catheter body is exposed when the inflatable balloon is partially inflated.

22. The laser catheter according to claim 10, wherein the portion of the interior of the catheter body is exposed when the inflatable balloon is deflated.

23. A laser catheter comprising:
a catheter body including a central axis, a distal end, a proximal end, and a cavity disposed within a periphery of the catheter body proximal to the distal end, wherein the cavity is cut through a portion of the periphery of the catheter body;
an inner tube including an aperture at the distal end of the catheter body, the inner tube positioned eccentric relative to the central axis of the catheter body;
a light guide disposed within the catheter body and extending from the proximal end to the distal end;
a balloon disposed within the cavity, wherein the balloon is configured to inflate inside the cavity, wherein a portion of the inflated balloon extends outside of the cavity proximal to the distal end of the catheter body, and wherein the inflated balloon is slidably coupled with the catheter body allowing the catheter body to move relative to the inflated balloon and allowing the inflated balloon to move relative to the catheter body in a longitudinal direction of the central axis, the inflated balloon remaining proximal to the distal end of the catheter body; and
a laser coupled with the light guide.

* * * * *